(12) United States Patent
DiCarlo et al.

(10) Patent No.: US 6,929,626 B2
(45) Date of Patent: Aug. 16, 2005

(54) INTRALUMINALLY PLACEABLE TEXTILE CATHETER, DRAIN AND STENT

(75) Inventors: Paul DiCarlo, Middleboro, MA (US); Christopher J. Elliott, Hopkinton, MA (US); William J. Shaw, Cambridge, MA (US); Brett Haarala, Framingham, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/342,950

(22) Filed: Jan. 15, 2003

(65) Prior Publication Data

US 2004/0138644 A1 Jul. 15, 2004

(51) Int. Cl.[7] .................................................. A61M 5/00
(52) U.S. Cl. ........................ 604/249; 604/249; 604/246; 604/523; 604/264
(58) Field of Search ................................ 604/246, 247, 604/249, 264, 523, 525, 527, 537, 544, 541, 103.01, 103.02, 167.01, 167.03; 600/435; 606/108, 193; 138/120, 118, 123

(56) References Cited

U.S. PATENT DOCUMENTS

| | | | |
|---|---|---|---|
| 4,549,879 A | 10/1985 | Groshong et al. |
| 4,671,796 A | 6/1987 | Groshong et al. |
| 4,701,166 A | 10/1987 | Groshong et al. |
| 4,899,787 A | 2/1990 | Ouchi et al. |
| 4,973,319 A | 11/1990 | Melsky |
| 4,981,477 A | 1/1991 | Schon et al. |
| 5,147,332 A | 9/1992 | Moorehead |
| 5,169,393 A | 12/1992 | Moorehead et al. |
| 5,201,722 A | 4/1993 | Moorehead et al. |
| 5,205,834 A | 4/1993 | Moorehead et al. |
| 5,224,938 A | 7/1993 | Fenton, Jr. |
| 5,290,263 A | 3/1994 | Wigness et al. |

(Continued)

FOREIGN PATENT DOCUMENTS

| | | |
|---|---|---|
| EP | 0 634 943 B1 | 3/1999 |
| WO | WO 93/20881 | 10/1993 |
| WO | WO 99/15219 | 4/1999 |
| WO | WO 13733 | 3/2000 |
| WO | WO 01/10492 | 2/2001 |
| WO | WO 01/66176 | 9/2001 |

*Primary Examiner*—Cris L. Rodriguez
(74) *Attorney, Agent, or Firm*—Hoffmann & Baron, LLP

(57) ABSTRACT

An intraluminally placeable tubular device includes an elongate hollow tubular member having a luminal surface and an exterior surface defining a wall portion therebetween. The hollow tubular member has an open proximal end and an opposed distal end. The wall portion has sufficient self-supporting rigidity to permit the device to be advanced through a body lumen during intraluminal placement. The tubular member includes yarns interconnected in a pattern defining opposed interior and exterior textile surfaces. At least one of the textile surfaces is the body fluid-contacting luminal surface or the body lumen-contacting exterior surface. A textile infusion and/or a textile aspiration valve is also provided. A percutaneously or orificially placeable catheter with such textile valves is provided.

23 Claims, 10 Drawing Sheets

U.S. PATENT DOCUMENTS

| | | |
|---|---|---|
| 5,338,295 A | 8/1994 | Cornelius et al. |
| 5,522,807 A | 6/1996 | Luther |
| 5,554,136 A | 9/1996 | Luther |
| 5,662,621 A | 9/1997 | Lafontaine |
| 5,683,410 A * | 11/1997 | Samson ..................... 606/194 |
| 5,704,926 A | 1/1998 | Sutton |
| 5,769,871 A * | 6/1998 | Mers Kelly et al. ........ 606/200 |
| 5,769,884 A | 6/1998 | Solovay |
| 5,807,349 A | 9/1998 | Person et al. |
| 5,899,892 A | 5/1999 | Mortier et al. |
| 5,928,203 A | 7/1999 | Davey et al. |
| 5,951,495 A | 9/1999 | Berg et al. |
| 5,954,651 A | 9/1999 | Berg et al. |
| 5,957,974 A | 9/1999 | Thompson et al. |
| 6,033,413 A * | 3/2000 | Mikus et al. ............... 606/108 |
| 6,077,258 A | 6/2000 | Lange et al. |
| 6,120,483 A | 9/2000 | Davey et al. |
| 6,212,422 B1 | 4/2001 | Berg et al. |
| 6,267,747 B1 * | 7/2001 | Samson et al. ........ 604/103.07 |
| 6,547,760 B1 * | 4/2003 | Samson et al. ........ 604/103.01 |
| 2001/0005552 A1 | 6/2001 | Berg et al. |
| 2001/0027307 A1 * | 10/2001 | Dubrul et al. .............. 604/508 |
| 2003/0100886 A1 * | 5/2003 | Segal et al. ................. 604/509 |

* cited by examiner

INTRALUMINALLY PLACEABLE TEXTILE CATHETER, DRAIN AND STENT

FIELD OF THE INVENTION

The present invention relates to an intraluminally placeable textile device for placement into a bodily lumen, such as a blood vessel or a bodily organ. More particularly, the present invention relates to a percutaneously or orificially pushable and placeable catheter, drainage tube or stent, such as a ureteral stent, having a textile body fluid contacting surface or a textile body lumen contacting surface.

BACKGROUND OF RELATED TECHNOLOGY

Percutaneously or orificially pushable and placeable devices, such as catheters, drainage tubes or ureteral stents, are often made from elongate hollow tubes of polymeric materials. Polymeric tubes, however, often have a high profile or large wall diameter to have sufficient rigidity to be percutaneously deliverable without collapse of the tube. In many cases, however, such large profiles are undesirable as causing patient discomfort or being excluded from use in small bodily lumens.

Polymeric tubes, for example catheters, have been reinforced with metallic supports, such as metallic coils or braids, to provide rigidity and pushablility while attempting to minimize the overall profile. The metallic supports, when used, are typically encased within the polymeric walls of the tube or catheter. While such supported tubes or catheters may have reduced profiles, their manufacture is expensive and complicated. Moreover, the tubular walls are often smooth polymeric surfaces making it difficult to coat its wall surfaces with a drug for drug delivery into a bodily lumen. For example, it is often difficult to maintain a catheter within a body lumen or organ for prolonged periods because in vivo access for drug delivery is often very difficult.

Furthermore, many applications exist where an infusion and/or aspiration valve is incorporated into the distal tip of a tube, such as a catheter. Such valves may be used for sampling bodily fluids or for transmitting fluids into a bodily lumen. Typically, the valves are slits within the polymeric wall of a tube or catheter. Such slits may be difficult to use in practice and may be difficult to keep clean during prolonged placement within a bodily lumen.

There is a need in the art for indwelling tubular devices, such as catheters, drainage tubes or stents, having low profiles. Moreover, there is a need in the art for such devices having aspiration and/or infusion values or drainage sites without the disadvantages of the prior art.

SUMMARY OF THE INVENTION

The present invention is a low-profile indwelling tubular device, such as a catheter, drainage tube or stent, having a textile pattern. The textile pattern results is useful for dispensing drugs therefrom while the device is placed within a bodily lumen, thereby offering greater indwelling times as compared to nontextile tubular devices, such as nontextile indwelling catheters. Furthermore, the tubular device may include textile aspiration and/or infusion valves which offer similar advantages of long term use within a bodily lumen without the disadvantages of the prior art polymeric valves.

In one aspect of the present invention an intraluminally placeable tubular device is provided. The device includes an elongate hollow tubular member having a body fluid-contacting luminal surface and a body lumen-contacting exterior surface defining a wall portion therebetween. The hollow tubular member has an open proximal end and an opposed distal end. The wall portion has sufficient self-supporting rigidity to permit the device to be advanced through a body lumen during placement. The tubular member includes yarns interconnected in a textile pattern defining a textile portion or surface. Desirably, at least one of the body fluid-contacting luminal surface or the body lumen-contacting exterior surface is the textile portion or surface. Useful yarn patterns include textile patterns, such as a braided pattern, a woven pattern, a knitted pattern, a filament wound pattern or combinations thereof. Desirably, the pattern is a braided textile pattern.

The wall portion is sufficiently self-supporting rigidity to permit the device to be advanced through a body lumen during intraluminal placement. The wall portion includes a substantially fluid-tight polymeric portion. Such a substantially fluid-tight polymeric portion may be formed by fusingly joining textile yarns. The device may further include a non-textile, polymeric hollow tubular member, such as a molded or extruded polymeric member of a biocompatible polymeric material, securably attached to the wall portion of the device.

Yarns useful with the device include synthetic yarns. Desirably, the synthetic yarns are biocompatible yarns, such as polyester yarns, polypropylene yarns, polyethylene yarns, polyurethane yarns and polytetrafluoroethylene yarns. Useful synthetic yarns include polyethylene terephthalate yarns. The synthetic yarns may be monofilament yarns, multifilament yarns, spun type yarns or combinations thereof. Moreover, at least one of the synthetic yarns may be a metallic yarn or a ceramic fiber.

The textile device may further include a second elongate hollow tubular member having a textile body fluid-contacting luminal surface or a textile body lumen-contacting exterior surface. Such a device is useful as an intraluminally placeable catheter.

The textile device may further include a wall portion having a porous wall portion defining a passage for fluid flow therebetween. Desirably, such a porous wall portion is also a textile portion. Such a textile device is useful as an intraluminally placeable drainage tube or stent, such as a ureteral stent. The stent may further include an outwardly shaped or a coiled-shaped proximal end or distal end.

The textile device may also include yarns which are coated with a bio-absorbable composition or a sealant composition. Desirably, such yarns releasably contain a drug or a bio-therapeutic agent, such as thrombo-resistant agents, antibiotic agents, anti-tumor agents, cell cycle regulating agents, their homologs, derivatives, fragments, pharmaceutical salts, and combinations thereof.

In another aspect of the present invention a valved catheter is provided. The catheter includes an elongate hollow tubular member having a luminal surface and an exterior surface defining a wall portion therebetween and having an open proximal end and an opposed distal end. The wall portion desirably has sufficient self-supporting rigidity to permit the catheter to be advanced through a body lumen. A portion of the wall having a textile valve includes interlocking yarns which engagingly abut one another to form a fluid tight textile pattern defining a closed quiescent state of the valve and which disengagingly separate to form open areas therebetween to form a non-fluid tight textile pattern defining an open state of the valve. Desirably, the open and closed states are responsive to application of a negative or positive pressure within the hollow tubular member.

The yarns forming the textile valve may have a fluid tight textile pattern which is a braided textile pattern having the interlocking yarns at a first longitudinal braid angle and have a non-fluid tight textile pattern which is braided textile pattern having the interlocking yarns at a second longitudinal braid angle. In this aspect of the present invention, the second longitudinal braid angle is different from the first longitudinal braid angle. The yarns in the fluid tight textile pattern may be braided at a longitudinal braid angle of greater than 90 degrees to provide an infusion valve where upon application of a positive pressure within the tubular member the longitudinal length of the textile valve increases resulting in the second longitudinal braid angle being less than the first longitudinal braid angle. Such an infusion valve remains in the closed state upon application of a negative pressure within the tubular member.

Alternatively, the yarns in the fluid tight textile pattern may be braided at a longitudinal braid angle of less than 50 degrees. Such a textile valve is an aspiration valve where upon application of a negative pressure within the tubular member the longitudinal length of the textile valve decreases resulting in the second longitudinal braid angle being greater than the first longitudinal braid angle. Desirably, the aspiration valve remains in the closed state upon application of a positive within the tubular member.

The valved catheter of the present invention may include both aspiration valves and infusion valves.

Yarns forming the valved catheter include biocompatible synthetic yarns, such as polyesters, polypropylenes, polyethylenes, polyurethanes, polytetrafluoroethylenes, metals and ceramics. The yarns may also be coated with a bio-absorbable composition or a sealant composition; or releasably contain a drug or a bio-therapeutic agent, such as thrombo-resistant agents, antibiotic agents, anti-tumor agents, cell cycle regulating agents, their homologs, derivatives, fragments, pharmaceutical salts, and combinations thereof.

A method of making an intraluminally pushable and placeable device includes the steps of (i) seamlessly interconnecting yarns in a textile pattern to form an elongate hollow tubular member having a body fluid-contacting luminal surface and a body lumen-contacting exterior surface defining a wall portion therebetween and having an open proximal end and an opposed distal end; and (ii) providing sufficient rigidity to the wall portion such the wall portion is self-supporting to permit the device to be advanced through a body lumen during placement. Desirably, the step of interconnecting the yarns includes braiding the yarns, weaving the yarns, knitting the yarns or filament winding the yarns. Moreover, the step of providing sufficient rigidity may further include heating a portion of the wall to fuse a portion of the yarns to form a polymeric nontextile wall portion.

The method may further include the step of making a textile valve by forming a textile valve in a portion of the tubular member by interlocking yarns which engagingly abut one another to form a fluid tight textile pattern defining a closed quiescent state of the valve and which disengagingly separate to form open areas therebetween defining a non-fluid tight textile pattern defining an open state of the valve.

Methods of using the devices of the present invention are also disclosed.

DETAILED DESCRIPTION OF THE INVENTION

The present invention is a textile device that is intraluminally pushable and placeable into a body lumen of a patient. As used herein, the phrase "body lumen" and its variants refer to a blood vessel, a bodily organ, or a bodily tube. Moreover, as used herein, the term "intraluminally" and its variants refer to within a body lumen. Such placement is typically performed through non-invasive or minimally invasive procedures. In other words, such devices are intraluminally or intratuballly placeable through percutaneous or orificial means. Examples of such devices include, but are not limited to, hemodialysis catheters, central venous catheters and catheters, stents or tubes for peritoneal dialysis, biliary drainage or drainage of malignant ascites.

Figure 1:
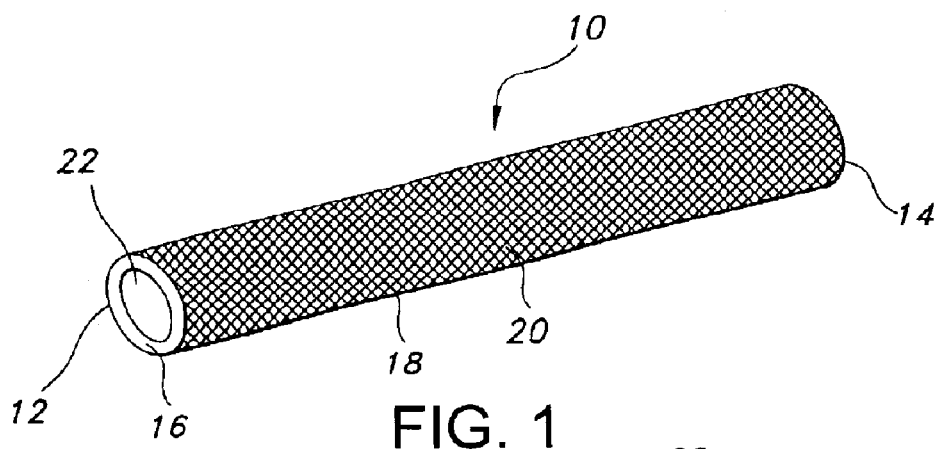
FIG. 1 is a perspective view of a percutaneously or orificially placeable tube of the present invention.

The textile device of the present invention includes a hollow, elongate tube, such as tube 10 as schematically depicted in FIG. 1. As used herein, the term "textile" and its variants refer to a structure of interlocked fibers formed by weaving, knitting, braiding or the like, and a "textile material" refers to a natural or synthetic fiber which can be woven, knitted, braided or the like into the textile tube of the present invention. Tube 10 has a proximal open end 12 and a distal end 14. The distal end 14 may be an open end or a closed end. Tube 10 has luminal textile surface 22 and exterior textile surface 18 defining a textile wall 16 therebetween. The tube 10 is constructed of interconnected yarns to provide a textile pattern 18. The tube 10 has sufficient self-supporting rigidity to permit the tube 10 to be advanced through a body lumen (not shown) during intraluminal placement.

The tube 10 is not, however, limited to a straight elongated shape. For example, tube 10 or portions of tube 10 may be inwardly or outwardly flared. Moreover, one or both ends 12 and 14 may include a varying shape, such as a flared shape (not shown), or a curved shape (not shown), such as a coiled shape or pig-tail shape, a J-shape and the like. Such a varying shape may be useful for, among other things, retaining the shaped tubular member with a bodily lumen, such as a kidney of a bladder.

Figure 2:
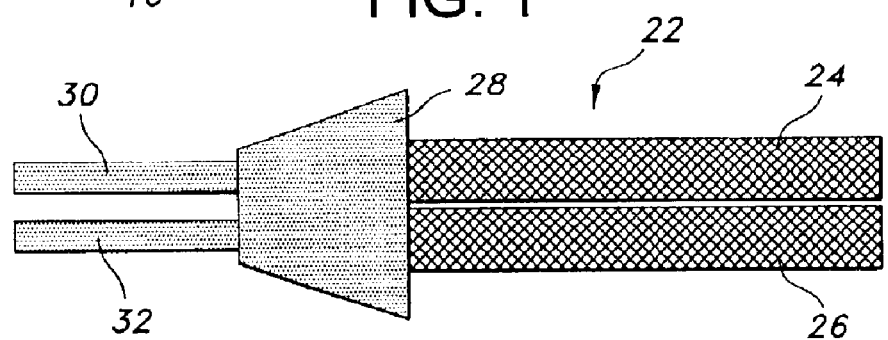
FIG. 2 is a side elevational view of a percutaneously or orificially placeable catheter of the present invention having textile corporeal tubes, nontextile excorporeal tubes and a nontextile connector joining the tubes.

Moreover, the present invention, however, is not limited to a single tube, such as tube 10. As depicted in FIG. 2, catheter 22 may include textile tubes 24 and 26 which are percutaneously or orificially placeable into a body lumen or body lumens. The textile tubes 24 and 26 may be securably attached to one and the other. Moreover connector 28 connects textile tubes 24 and 26 to excorporeal tubes 30 and 32, respectively. Connector 28 may be a molded, extruded or otherwise formed nontextile connector. Excorporeal tubes 30 and 32 are not typically implanted into the body, but generally serve as conduits to external devices, such as hemodialysis devices or drug delivery devices.

Figure 3:
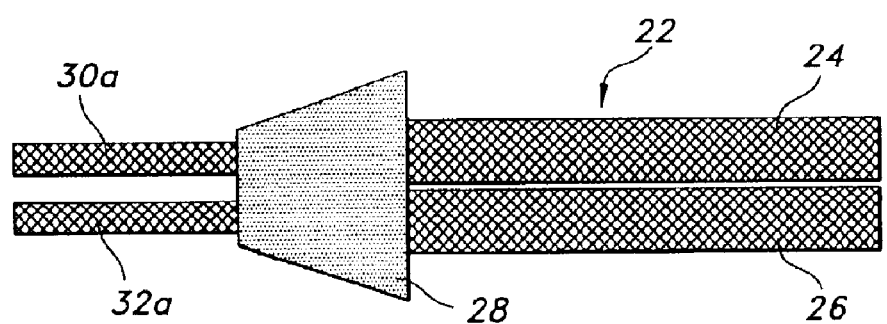
FIG. 3 is a side elevational view of a percutaneously or orificially placeable catheter of the present invention having textile corporeal tubes, textile excorporeal tubes and a nontextile connector joining the tubes.
Figure 4:
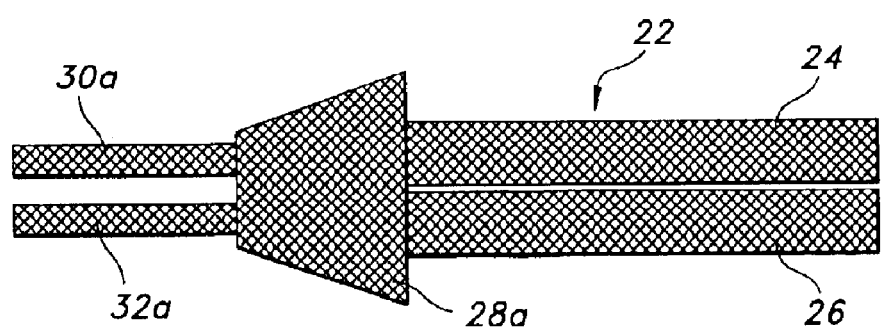
FIG. 4 is a side elevational view of a percutaneously or orificially placeable catheter of the present invention having textile corporeal tubes, textile excorporeal tubes and a textile connector joining the tubes.

The tubes 30 and 32 are depicted in FIG. 2 as polymeric or otherwise nontextile tubes. As used herein, the term "non-textile" and its variants refer to a structure formed by nontextile methods, such as extruding, molding, depositing, solidifying, and polymerizing of materials. The present invention, however, is not limited to the use of nontextile tubes 30 and 32. As depicted in FIG. 3, the excorporeal tubes may be textile tubes 30a and 32a. Furthermore, as depicted in FIG. 4, the excorporeal tubes may be textile tubes 30a and 32a, and the connector may be a textile connector 28a.

The different textile and nontextile components may be secured to one and the other by any suitable means. For example, different textile components may be sewn together, stapled together, adhesively secured together or formed as a unitary textile structure having different sizes, shapes and number of branches. Desirably, such a unitary textile structure is a seamless textile structure providing fluid tight transition regions between different textile shapes or geometries. Nontextile components may be included and formed into a unitary structure through molding or extruding processes. Alternatively, nontextile components may be joined to other nontextile or textile components by any suitable means, such as, but not limited to, adhesive securement or encapsulation.

Figure 5:
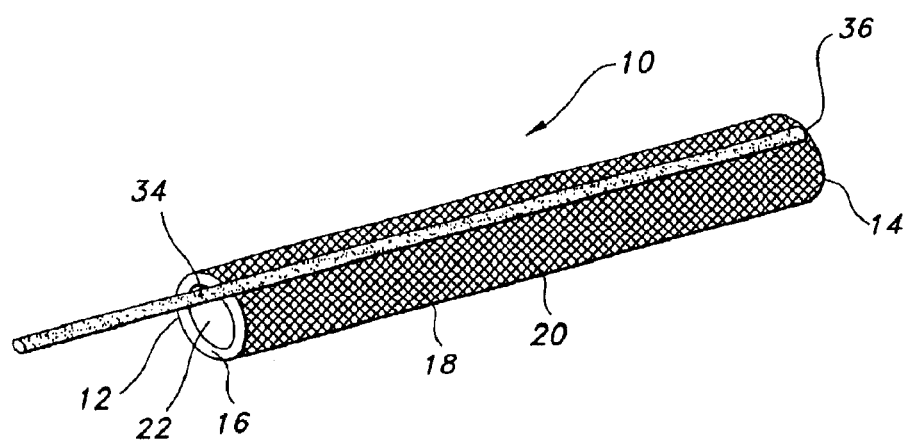
FIG. 5 is a perspective view of the tube of FIG. 1 having a guidewire.

As depicted in FIG. 5, the tube 10 may include a guidewire 34. The guidewire 34 may be secured to textile wall 16 near the distal end 14, the proximal end 12 or at portions there between. The guidewire 34 may be releasably secured to tube 10 or may be slidably engaging and/or disengaging from the textile tube 10. The use of guidewire 34 not only may facilitate the percutaneous or orificially placement by providing a steering mechanism to a desired body site, but may also provide pushablility to the tube 10, especially when the guidewire 34 is attached to the distal end 14 and/or the proximal end 12 of tube 10.

Guidewire 34 may be any guidewire as is known in the art. Guidewire 34 is typically an elongated, relatively rigid cylindrical member. Guidewire 34 may be constructed of any material, but is preferably constructed of metal, such as stainless steel, gold, platinum, and metal alloys such as cobalt-based alloys or titanium alloys, for example, nickel-titanium shape memory alloys (i.e., nitinol), titanium-aluminum-vanadium alloys and titanium-zirconium-niobium alloys.

Moreover, guidewire 34 may have a constant stiffness or flexibility along the entire length thereof, or may have portions of varying stiffness and flexibility, such as an area of increased flexibility at guidewire tip 36. Guidewire 34 may further include a coating along a portion or the entire length thereof, such as a lubricious or frictionless coating material. Guidewire 34 may further be provided with a radiopaque portion, for example in the form of a radiopaque coating on a portion of the guidewire, or by constructing a portion of the guidewire out of a radiopaque material.

Figures 6, 7:
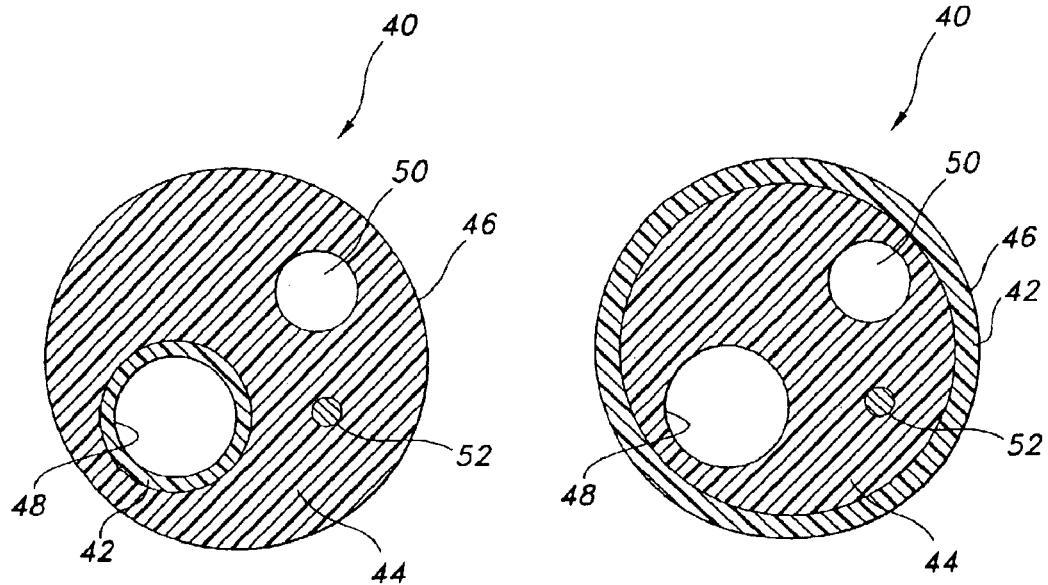
FIG. 6 is a cross sectional view of a percutaneously or orificially placeable tube having an interior textile lumen and an exterior nontextile surface.
FIG. 7 is a cross sectional view of a percutaneously or orificially placeable tube having an interior polymeric lumen and an exterior textile surface.

As depicted in FIG. 6, the intraluminally placeable device 40 of the present invention may include an elongate textile portion 42 and an elongate nontextile portion 44. Textile portion 42 is an elongate hollow tubular member and is shown as being within the nontextile portion 44 in FIG. 6. In such a case a body lumen-contacting exterior surface 46 is a nontextile surface, and a body fluid-contacting luminal surface 48 is a textile surface. The nontextile portion 44 may include a conduit 50 which may have a similar or different shape or internal diameter from the textile portion 42. Conduit 50 may be a body fluid contacting conduit, a fluid transmitting conduit or a conduit for slidably moving the device 40 over a guidewire (not shown). Alternatively, a guidewire 52 may be securably attached within the nontextile portion 44. The guidewire 52 may be suitably constructed as the above-described guidewire 34.

The nontextile portion 44 is desirably formed by fusing textile yarns (not shown) to form a substantially fluid tight nontextile portion 44. Moreover, the nontextile portion 44 provides sufficient rigidity such that device 40 is self-supporting and pushable through body lumens. As used herein, the term "fuse" and it variants refer to a polymeric textile yarns that can be joined together by melting or partially melting the yarns forming a nontextile polymeric portion. The fusing of the textile yarns may be suitably achieved by supplying thermal energy or heat to the nontextile portion 44 while supplying cooling to the textile portion 42. For example, a rod (not shown) having a cooling means could be placed within the area of device 40 represented by the body fluid-contacting luminal surface 48. The rod could be hollow and have a cooling medium, such as cold water and the like, flowing therethrough to keep textile portion 42 cool. The nontextile portion 44 may suitably be formed by placing the device 40 with a heatable die or tube (not shown) and supplying heat thereto. The present invention, however, is not limited to any particular type of cooling and/or heating techniques and any suitable technique may be used.

The yarns initially forming the nontextile portion 44 may partially or substantially maintain their textile orientation after being fused or melted to form the substantially fluid-tight wall portion. Additionally, the yarns initially forming the nontextile portion 44 may be substantially fused or melted rendering the polymeric materials of the yarns in a commingled, nontextile state. Moreover, the nontextile portion 44 may contain portions that are substantially fused, partially fused, and degrees of fusing therebetween. For example, the exterior portions of nontextile portion 44, which may be proximal to heating sources or heating media may be substantially fused defining a polymeric, non-textile portion while portion of the nontextile portion 44 proximal to the textile portion 42 may be partially fused.

Furthermore, nontextile portion 44 may be constructed of any suitable biocompatible materials, such as, but not limited to, polymeric polymers and materials, including fillers such as metals, carbon fibers, glass fibers or ceramics. Useful polymeric materials may include, for example, olefin polymers. Non-limiting examples of useful polymeric materials include polyethylene, polypropylene, polyvinyl chloride, polytetrafluoroethylene, including expanded polytetrafluoroethylene (ePTFE), fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, and copolymers and combinations thereof. The polymeric materials set forth above are intended to be exemplary only and should not be construed to limit in any way the types of materials which may be used in the present invention. The nontextile portion 44 of the present invention may be suitably made by the above-described heat-fusing, but may also include portions made by extruding, molding, coating or otherwise processing biocompatible polymeric materials. The nontextile portion 44 may also be reinforced As depicted in FIG. 7, the intraluminally placeable device 40 of the present invention may include the textile portion 42 covering or encompassing portions of the nontextile portion 44. In such a case a body lumen-contacting exterior surface 46 is a textile surface, and a body fluid-contacting luminal surface 48 is a nontextile surface. The nontextile portion 44 may include a conduit 50 or a guidewire 52.

Figure 8:
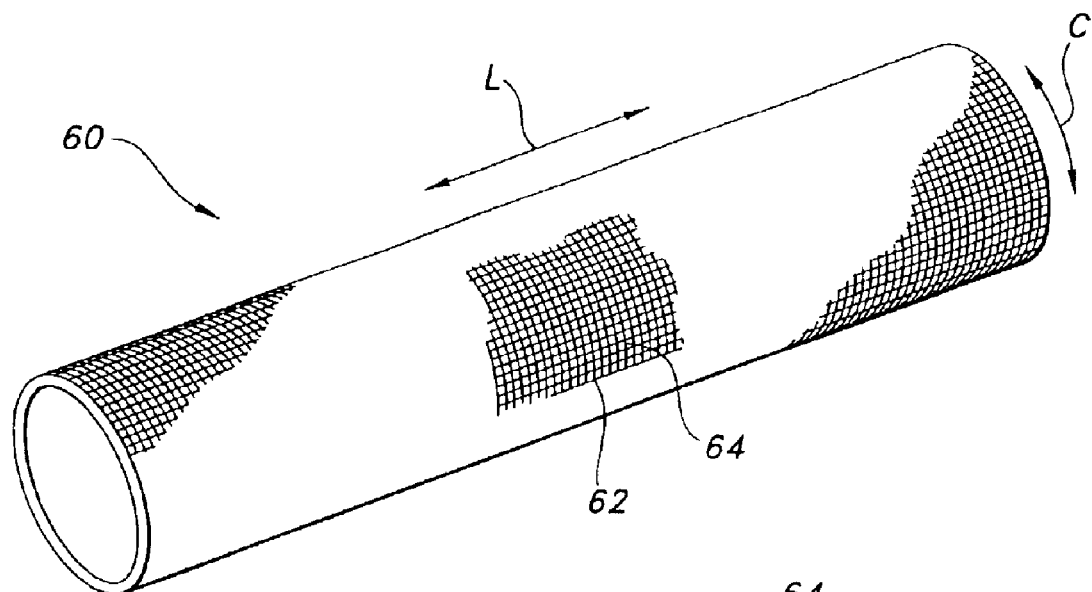
FIG. 8 is a perspective view of a woven tubular textile useful in the present invention.
Figure 9:
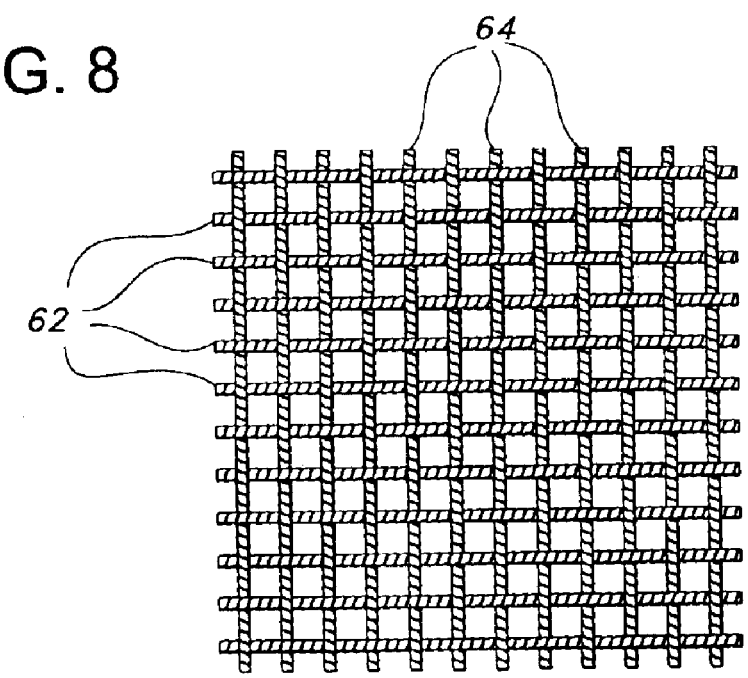
FIG. 9 is a schematic of a conventional weave pattern useful in the woven tubular textile of FIG. 8.

The textile portions of the present invention may be made from any suitable biocompatible synthetic yarns, including synthetic yarns, interconnected in virtually any textile construction, including weaves, knits, braids, filament windings, fiber spinning and the like. Referring to the drawings and, in particular to FIGS. 8 and 9, an elongate woven hollow tubular textile 60 is shown. Any known weave pattern in the art, including, simple weaves, basket weaves, twill weaves, velour weaves and the like may be used. The weave pattern includes warp yarns 62 running along the longitudinal length (L) of the woven textile and fill yarns 64 running around the circumference (C) of the textile. The warp yarns 62 are positioned approximately 90 degrees relative to the fill yarns 64. The textile typically flows from the machine in the warp direction. A simple weave is shown in FIG. 9 where adjacent warp yarns 62 and adjacent fill yarns 64 interlock or interconnect with one and the other.

Figure 10:
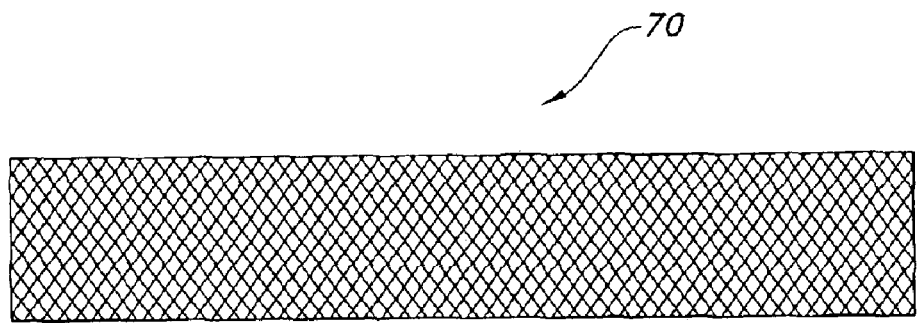
FIG. 10 is a side elevational view of a braided tubular textile useful in the present invention.
Figure 11:
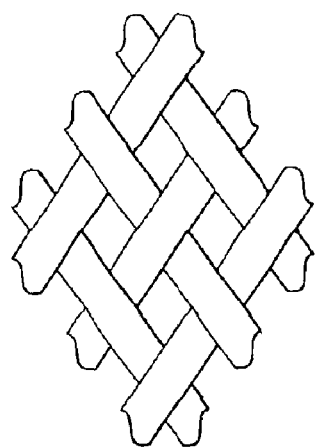
FIG. 11 is a schematic of a diamond braid useful in the braided tubular textile of FIG. 10.
Figure 12:
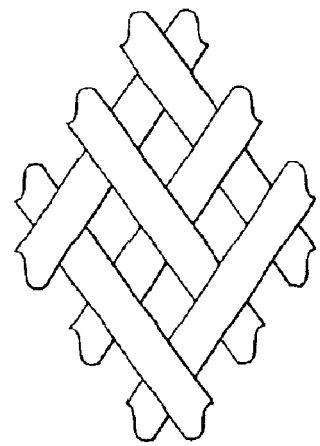
FIG. 12 is a schematic of a regular braid useful in the braided tubular textile of FIG. 10.
Figure 13:
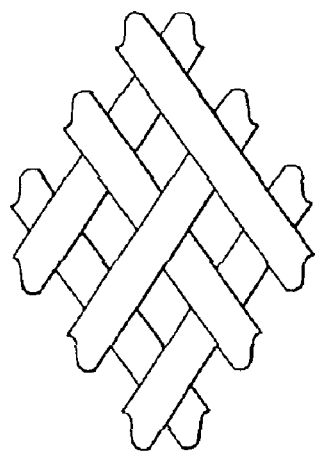
FIG. 13 is a schematic of a hercules braid useful in the braided tubular textile of FIG. 10.

Braiding may also be used as shown, for example, in FIGS. 11 through 13 to form a hollow tubular braided textile portion 70 as depicted in FIG. 10. As depicted in FIG. 10, braiding of yarns includes the interlacing of at least two yarn systems such that the paths of the yarns are diagonal to the fabric delivery direction, forming either a flat or tubular structure. Useful braids include, but are not limited to, a diamond braid having a 1/1 intersection repeat as shown in FIG. 11, a regular braid having a 2/2 intersection repeat as shown in FIG. 12, or a Hercules braid having a 3/3 intersection repeat as shown in FIG. 13. Moreover, a triaxial braid may also be used. A triaxial braid, not shown, has at least one yarn that typically runs in the longitudinal direction or axial direction of the textile portion to limit yarn movement. The axial or longitudinal yarn is not interlaced or interwound with the other braid yarn, but is trapped between the different sets of yarns in the braided structure. Moreover, an interlocking three-dimensional braided structure or a multi-layered braided structure is also useful. A multi-layered braided structure is defined as a structure formed by braiding wherein the structure has a plurality of distinct and discrete layers. These layers may be bound by interlocking yarns or by adhesive laminates, sewing or the like.

Figure 14:
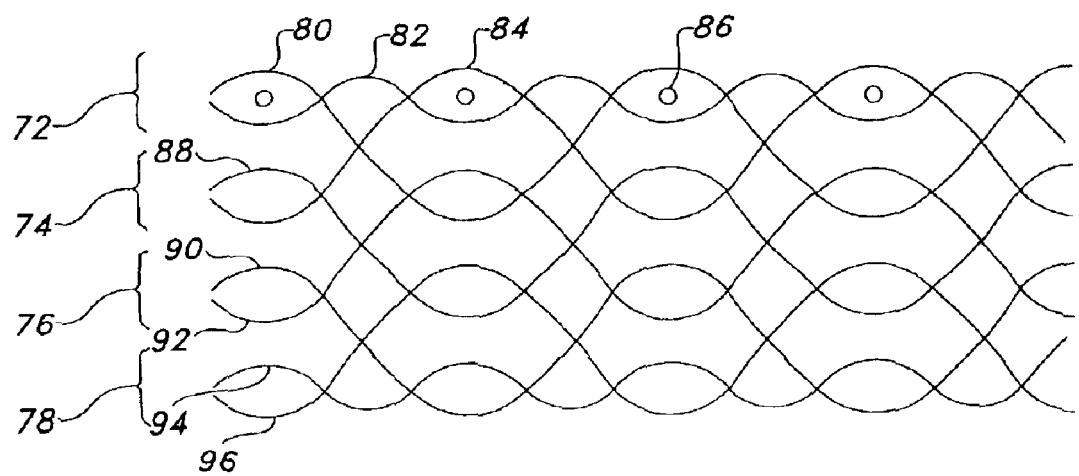
FIG. 14 is a cross-sectional view of a portion of a multi-layered interlocked three-dimensional braided textile formed in accordance with an embodiment of the present invention.

An interlocking three-dimensional braid, as shown in FIG. 14, may be used and is defined as a braided structure having at least two layers, whereby a yarn is interbraided from a first layer into a contiguous second layer to interlock the layers of the multi-layer braid. A braiding machine capable of forming the interlocked three-dimensional braid used to form the textile tube of the present invention is described in International Patent Publication No. WO 91/10766, which is incorporated herein by reference. Referring to FIG. 14, the textile portion includes four layers, 72, 74, 76 and 78, with each layer having at least one interlocking yarn from a contiguous layer. The interlocking yarns are braided into the structure so that the yarn forms part of the first layer, as well as being part of the contiguous layer by forming the interlock. Within each layer, a segment of the braid is formed by an interlocking yarn from a contiguous layer, the layers being interbraided together. The interlocking yarns couple the multiple layers together to form a three-dimensional braid. In FIG. 14, the first layer 72 forms the outer layer of the interlocking three-dimensional braided structure. The outer layer is formed from yarn 82 which is exclusively braided into the first layer along with yarn 80 which is interbraided into a second layer which is contiguous with the first layer and yarn 84 which is interbraided from the second layer up into the first layer. Second layer 74 is formed from segments of four yarns 80, 84, 88 and 92 which are interbraided. The next contiguous layer 76 is formed from segments of four yarns 88, 90, 92 and 96 interbraided to form an inner layer in the multilayered structure. Layer 78 is formed in similar fashion, having three yarns 90, 94 and 96 which are interbraided.

Generally, a braided structure is formed having a braid angle from about 54.5° to about 90° with respect to the longitudinal axis of the braided structure, desirably about 54.5° to about 75°. The yarns of the braid tend to seek equilibrium at a braid angle of about 54.5°, which is a neutral angle for tubular vessels under pressure. Thus, when the braid angle is larger than the neutral angle, when pressure is exerted from within, for example due to fluid flow, the yarns will tend to scissor and decrease the braid angle thereby elongating or stretching the braided structure in order to reach the neutral angle.

Figure 15:
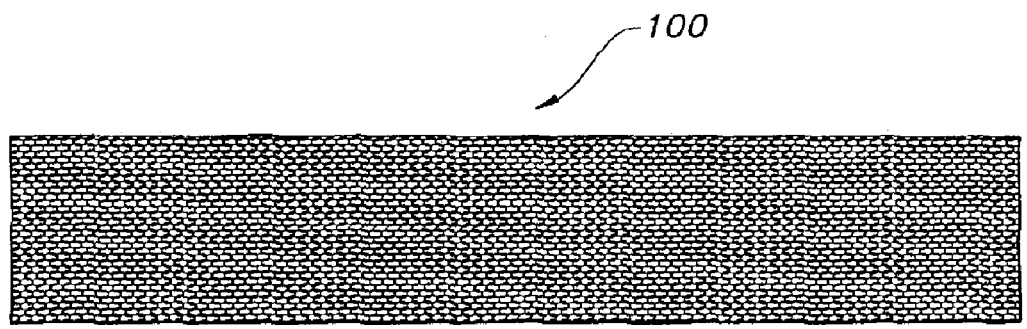
FIG. 15 is a side elevational view of a knitted tubular textile useful in the present invention.
Figure 16:
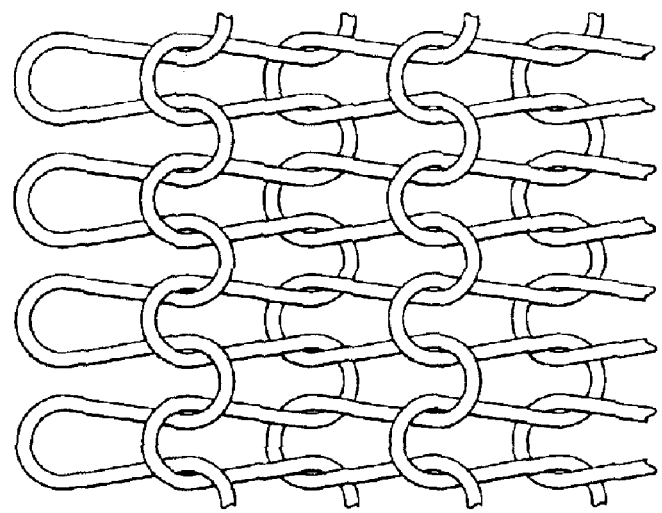
FIG. 16 is a schematic of a jersey weft knit useful in the knitted tubular textile of FIG. 15.

Additionally, a knitted textile member 100, as shown in FIGS. 15 and 16, may be used. Knitting involves the interlooping of one yarn system into vertical columns and horizontal rows of loops called wales and courses, respectively, with fabric coming out of the machine in the wale direction. A nonlimiting example of a knitted textile pattern, such as jersey weft knit, is depicted in FIG. 16. Other knit patterns, such as double tricot warp knit, may suitably be used.

Figure 17:
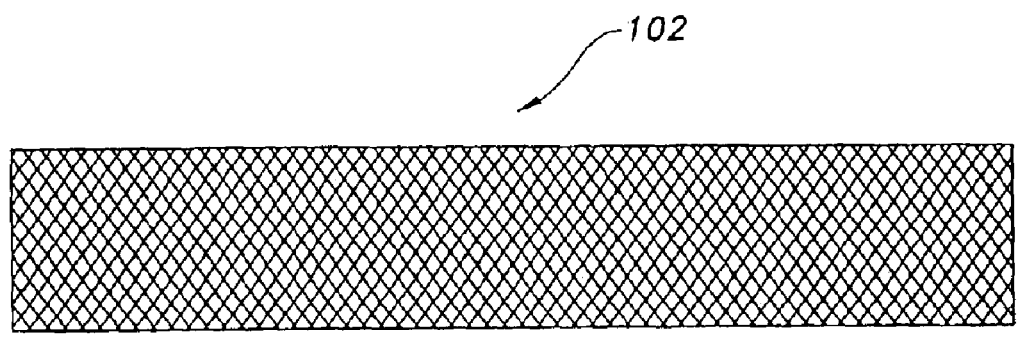
FIG. 17 is a side elevational view of a filament wound tubular textile useful in the present invention.
Figure 18:
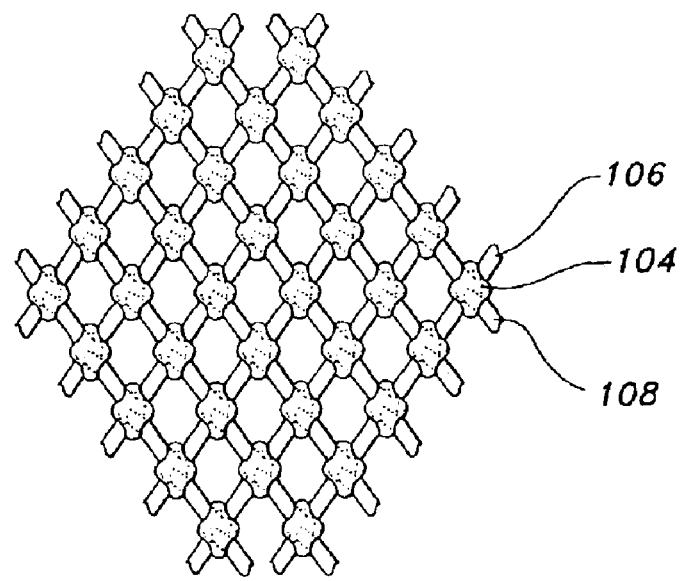
FIG. 18 is an enlarged detail of FIG. 17.

A filament wound textile member 102, as shown in FIGS. 17 and 18, may also be used where a yarn is transferred from one package to a mandrel to form a hollow tubular member that is wrapped with the yarn in both directions to provide a biaxial reinforcement. A helix angle of about 55 degrees is typically used. To hold the yarns in place, they are passed through a solution of solvated polyurethane elastomer, such a BIOMARK® solution, commercially available from Johnson & Johnson. The solvent is removed, causing the polyurethane 104 to dry and glue the yarns 106 and 108 together.

Figure 19:
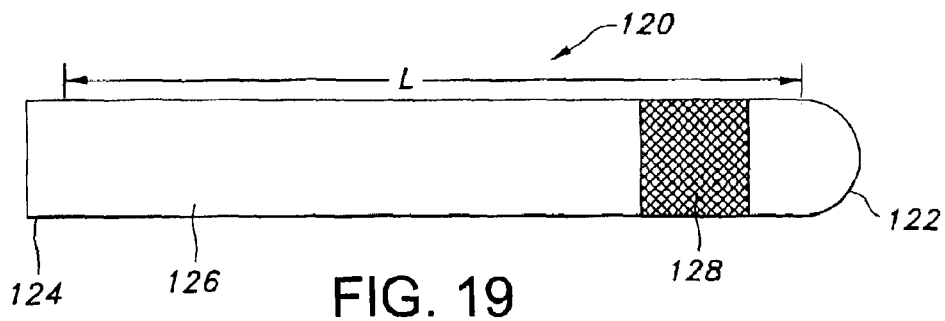
FIG. 19 is a side elevational view of a catheter tube having a textile valve formed in accordance with an embodiment of the present invention.

The intraluminally placeable devices of the present invention may also include a valve for delivery of a fluid into a body lumen or withdrawal of a body fluid from the body lumen. As depicted in FIG. 19, a catheter 120, which is a hollow intraluminally placeable device, has a wall portion 126 defining an open proximal end 124 and a distal end 122. Desirably, wall portion 126 is fluid-tight or substantially fluid-tight wall portion. The longitudinal or axis of catheter 120 is depicted by vector L. The distal end 122 is shown as a closed end, but the invention is not so limited. The distal end 122 may be closed, fully open or partially open. The catheter 120 includes a textile valve 128.

Textile valve 128 is formed from any of the above-discussed textile patterns, such as a braid, a weave, a knit or a filament wound textile pattern. The textile valve 128 is fluid tight or substantially fluid tight in a closed position. In the closed or quiescent position the yarns abuttingly engage one and the other to form a fluid tight or substantially fluid tight wall portion. Upon the application of a pressure within the catheter 120, the yarns disengage from one and the other to form open spaces therebetween and define a non-fluid tight wall portion. These yarns in the open position remain interlocked in the textile pattern and slidingly disengage to form the open spaces therebetween. The textile valve of the present invention opens from it closed, fluid tight, quiescent state upon the application of a negative or positive pressure, i.e., a pressure smaller or greater than the nominal luminal pressure in which the catheter has been intraluminally placed.

Figure 20:
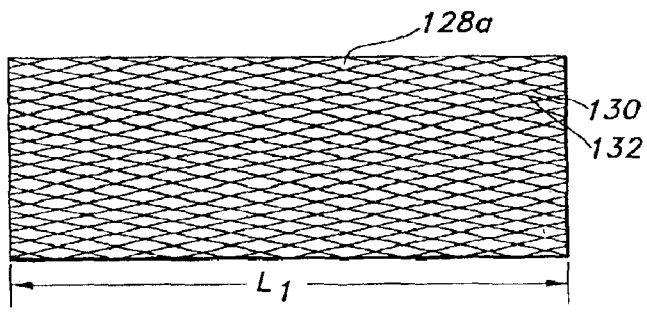
FIG. 20 is an enlarged view of a portion of an embodiment of the textile valve of FIG. 19 being in a substantially fluid tight textile pattern.
Figure 21:
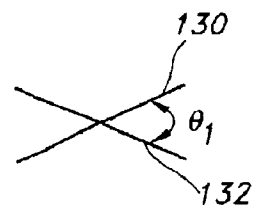
FIG. 21 is an enlarged view of interlocking yarns of a portion of the textile valve of FIG. 20.

FIG. 20 is an enlarged view of a portion of the textile valve 128. In this embodiment the textile valve portion 128a is depicted as a fluid tight or substantially fluid tight braided textile. The braided yarns, such as yarns 130 and 132, are braided such that the longitudinal braid angle, $\theta_1$, as depicted in FIG. 21, is less than about 54.5 degrees. Desirably, the longitudinal braid angle, $\theta_1$, is less than about 50 degrees. Longitudinal braid angles from about 5 degrees to about 50 degrees are also useful. Moreover, longitudinal braid angles from about 15 degrees to about 40 degrees are also useful.

Figure 22:
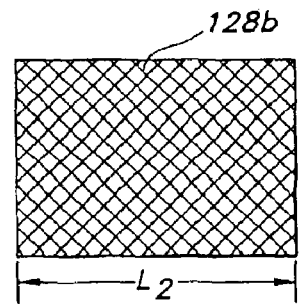
FIG. 22 is an enlarged view of a portion of the textile valve of FIG. 20 being in a substantially non-fluid tight textile pattern.

Upon application of pressure within the catheter 120, the yarns of textile valve portion 128a experience a stress or force from the pressure. When a negative pressure, i.e., a pressure below the luminal pressure within a bodily lumen, is applied within the catheter 120, the yarns slidingly disengage to increase the longitudinal braid angle to a value greater than $\theta_1$. The increasing braid angle results in open spaces between the yarns. The yarns will tend to disengage until an angle of about 54.5 degrees is reached or until otherwise constrained. As depicted in FIGS. 20 and 22, the length, $L_1$, of the textile portion 128a in the closed position is greater than the length, $L_2$, of the textile portion 128b in the open position. In other words, the textile valve portion 128a with a low longitudinal braid angle, i.e., a $\theta_1$ of less than about 50 degrees, will tend to reduce its longitudinal length as the valve moves from its closed or quiescent position to its open position. Correspondingly, the diameter (not shown) of the textile valve will expand slightly as the textile valve moves from its closed position to the open position.

The textile valve portion 128b moves from its open position to the closed position of textile valve portion 128a upon removal of the negative pressure within the catheter 120. A positive pressure may also be used to facilitate the closing of textile valve portion 128b. During closing of the textile valve portion 128b the yarns return to the braid angle $\theta_1$ and the longitudinal length, $L_1$, of the closed position, i.e., textile valve portion 128a.

Upon application of a positive pressure, i.e., a pressure above the luminal pressure within a bodily lumen, the yarns of textile valve portion 128a remain abuttingly engaged in a fluid tight or substantially fluid tight position or state and the so constrained portion 128a cannot substantially decrease the longitudinal angle below $\theta_1$ or substantially increase the longitudinal length greater than $L_1$.

The textile valve portion 128a may be referred to as an aspiration valve. Such aspiration valves may be used to sample body fluids because they open upon application of a negative pressure within the hollow intraluminal device.

Figure 23:
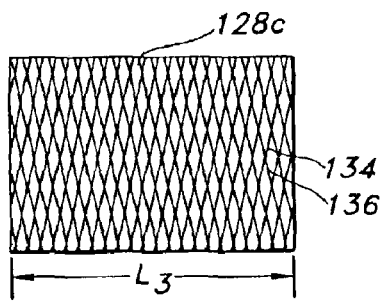
FIG. 23 is an enlarged view of a portion of another embodiment of the textile valve of FIG. 19 being in a substantially fluid tight textile pattern.
Figure 24:
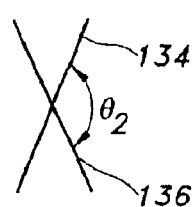
FIG. 24 is an enlarged view of interlocking yarns of a portion of the textile valve of FIG. 23.

FIG. 23 is an enlarged view of another embodiment of a portion of the textile valve 128. In this embodiment the textile valve portion 128c is depicted as a fluid tight or substantially fluid tight braided textile. The braided yarns, such as yarns 134 and 136, are braided such that the longitudinal braid angle, $\theta_2$, as depicted in FIG. 24, is greater than about 54.5 degrees. Desirably, the longitudinal braid angle, $\theta_2$, is greater than about 90 degrees. Longitudinal braid angles from about 90 degrees to about 170 degrees are also useful. Moreover, longitudinal braid angles from about 90 degrees to about 120 degrees are also useful.

Figure 25:
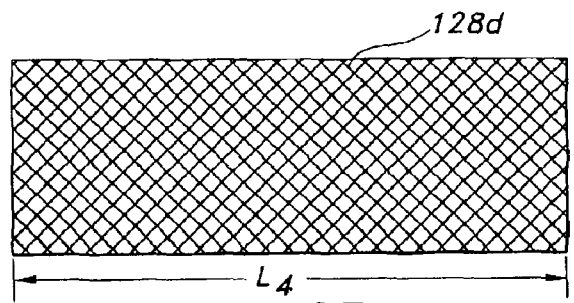
FIG. 25 is an enlarged view of a portion of the textile valve of FIG. 23 being in a substantially non-fluid tight textile pattern.

Upon application of pressure within the catheter 120, the yarns of textile valve portion 128c experience a stress or force from the pressure. When a positive pressure is applied within the catheter 120, the yarns slidingly disengage to decrease the longitudinal braid angle to a value less than $\theta_2$. The decreasing braid angle results in open spaces between the yarns. The yarns will tend to disengage until an angle of about 54.5 degrees is reached or until otherwise constrained. As depicted in FIGS. 23 and 25, the length, $L_3$, of the textile portion 128c in the closed position is less than the length, $L_4$, of the textile portion 128d in the open position. In other words, the textile valve portion 128c with a high longitudinal braid angle, i.e., a $\theta_2$ of greater than about 90 degrees, will tend to increase its longitudinal length as the valve moves from its closed or quiescent position to its open position. Correspondingly, the diameter (not shown) of the textile valve will decrease slightly as the textile valve moves from its closed position to the open position.

The textile valve portion 128d moves from its open position to the closed position of textile valve portion 128c upon removal of the positive pressure within the catheter 120. A negative pressure may also be used to facilitate the closing of textile valve portion 128d. During closing of the textile valve portion 128d the yarns return to the braid angle $\theta_2$ and the longitudinal length, $L_3$, of the closed position, i.e., textile valve portion 128c.

Upon application of a negative pressure the yarns of textile valve portion 128c remain abuttingly engaged in a fluid tight or substantially fluid tight position or state and the so constrained portion 128c cannot substantially increase the longitudinal angle above $\theta_2$ or substantially decrease the longitudinal length less than $L_3$.

The textile valve portion 128c may be referred to as an infusion valve. Such infusion valves may be used to transmit fluids into a body lumen because they open upon application of a positive pressure within the hollow intraluminal device.

Any type of biocompatible textile product can be used as yarns for the textile portion or portions of the intraluminally pushable and placeable device of the present invention. Of particular usefulness in forming the textile portions of the present invention are synthetic biocompatible materials such as synthetic polymers. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, natural silk and polytetrafluoroethylenes. Moreover, at least one of the synthetic yarns may be a metallic yarn or a glass or ceramic yarn or fiber. Useful metallic yarns include those yarns made from or having stainless steel, platinum, gold, titanium, tantalum and Ni—Co—Cr-based alloy. The yarns may further comprise carbon, glass or ceramic fibers.

The yarns may also be a combination of polymeric materials, such as yarns having different melting temperatures. In such a case, as the textile device is submitted to heating or thermal energy case certain yarns, such as yarns having lower melting temperatures, can fusibly join to form the polymeric or non-textile portion of the device while yarns of a higher melting temperature remain in their textile pattern forming the textile portion of the device of the present invention. An example of low melting temperature yarns are yarns having fusible biocompatible staple fibers combined with low melting copolyester or polyethylene, as disclosed in U.S. Pat. No. 5,282,846 to Schmitt, the contents of which are incorporated herein by reference. Such yarns have components having melting temperatures from about 110° C. to about 200° C. Moreover, the different classes of useful biocompatible synthetic yarns also have a wide range of melting temperatures. For example, approximate and non-limiting ranges of melting temperatures include about 220° C. to about 280° C. for polyesters, including about 240° C. to about 250° C. for PET polyesters, about 130° C. to about 170° C. for polypropylenes, about 105° C. to about 135° C. for polyethylenes, about 150° C. to about 230° C. for polyurethanes and typically exceeding 300° C. for polytetrafluoroethylenes. These melting temperatures are non-limiting and can often be varied with the addition of additional materials, including other polymers or copolymers.

The yarns may be of the monofilament, multifilament, spun type or combinations thereof. The yarns may also be textured or non-textured, shrunk or non-shrunk. Desirably, the yarns are monofilament yarns, multifilament yarns having a filament count of about 10 to about 200 or combinations thereof. More desirably, the yarns are monofilament yarns.

The yarns used in forming the textile portions of the present invention may be flat, twisted, textured or combinations thereof. Furthermore, the yarns may have high, low or moderate shrinkage properties or combination of different shrinkage properties. Additionally, the yarn type and yarn denier can be selected to meet specific properties desired for the device, such as porosity and flexibility. The yarn denier represents the linear density of the yarn (number of grams mass divided by 9,000 meters of length). Thus, a yarn with a small denier would correspond to a very fine yarn whereas a yarn with a larger denier, e.g., 1000, would correspond to a heavy yarn. Yarns useful in the inventive devices have a non-limiting denier range from about 20 to about 1500.

Generally, tubular textile portions are manufactured into a single long tube and cut to a predetermined length. The textile portions are cleaned and rinsed with deionized water. The portions may then placed over a mandrel and heat set to precisely set the diameter and shape and to remove any creases or wrinkles. Typically heat conditioning is carried out at a temperature range from about 125° C. to about 225° C. using a convection oven for a time of 20 minutes. Any known means for heating the structure may be used. Moreover, as described above, the textile device of the present invention may include fusible yarns which may form the polymeric portion of the present invention by melting at these temperatures.

The textile portion of the present invention may be coated with a bio-absorbable coating, such as collagen, albumin, elastin and the like. Such coatings are known in the art and may be desirable in certain vascular or endovascular applications to seal the textile portion and thereby prevent blood loss in the early stages of placement. Other coatings which may be used include those disclosed in U.S. Pat. No. 5,851,229, which is incorporated herein, and which discloses a sealant composition that includes at least two polysaccharides in combination to form a hydrogel or solgel. Additionally, latex, silicone and elastomeric compositions are useful as sealant compositions. Sealant compositions may include a bioactive agent and or be cross-linked subsequent to the application of these compositions to the substrate surface. Additionally, U.S. Pat. No. 5,209,776, incorporated herein, discloses a composition that includes a first protein component that is preferably collagen and a second protein-supporting component that can be a proteoglycan, a saccharide or a polyalcohol.

Moreover, the textile portions or the yarns forming the textile portions of the present invention may be coated or otherwise incorporated therein with one or more agents, such as bio-therapeutic agents. The textile portions of the device may be coated or otherwise incorporated with bio-therapeutic agents after being formed by the above-described textile techniques. Alternatively, the yarns may have bio-therapeutic agents incorporated therewith prior to forming the textile portions. Moreover, combinations of these techniques may be used. Furthermore, different yarns may have different bio-therapeutic agents incorporated therein. For example, certain yarns may be coated with an anti-fibrin agent and other yarns may be coated with an anti-bacterial agent. The differently coated yarns may be used to form different portions of the textile device. For example, yarns forming the textile portion may be coated with bio-therapeutic agents while yarns, such as fusible yarns, forming the polymeric portion may not be so coated. Still furthermore, yarns may be formed from fibers having different bio-therapeutic agents incorporated therein. These bio-therapeutic agents include pharmaceutical agents. Such materials may be used to target therapeutic agents to specific sites of the body.

Any drug or bio-therapeutic agent may be coated or incorporated into the textile yarns or textile portions of the present invention. Examples of suitable drugs or bio-therapeutic agents may include, without limitation, thrombo-resistant agents, antibiotic agents, anti-tumor agents, cell cycle regulating agents, their homologs, derivatives, fragments, pharmaceutical salts, and combinations thereof.

Useful thrombo-resistant agents may include, for example, heparin, heparin sulfate, hirudin, chondroitin sulfate, dermatan sulfate, keratin sulfate, lytic agents, including urokinase and streptokinase, their homologs, analogs, fragments, derivatives and pharmaceutical salts thereof.

Useful antibiotics may include, for example, penicillins, cephalosporins, vancomycins, aminoglycosides, quinolones, polymyxins, erythromycins, tetracyclines, chloramphenicols, clindamycins, lincomycins, sulfonamides, their homologs, analogs, fragments, derivatives, pharmaceutical salts and mixtures thereof.

Useful anti-tumor agents may include, for example, paclitaxel, docetaxel, alkylating agents including mechlorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; enzymes including asparaginase; and hormones including tamoxifen and flutamide; their homologs, analogs, fragments, derivatives, pharmaceutical salts and mixtures thereof.

Useful anti-viral agents may include, for example, amantadines, rimantadines, ribavirins, idoxuridines, vidarabines, trifluridines, acyclovirs, ganciclovirs, zidovudines, foscarnets, interferons, their homologs, analogs, fragments, derivatives, pharmaceutical salts and mixtures thereof Axial yarns are added in some cases to limit a textile structure from stretching beyond a desired amount, and thereby significantly reducing the potential for scissoring action of the yarns. This scissoring or shearing action may detrimental in certain instances. The scissoring action of the strands tends to prevent the tissue and blood vessels from infiltrating the pores of the structure. Additionally, an axial yarn may be dyed and inserted into the textile structure subsequent to or during the braiding process.

The intraluminally placeable device of the present invention may also include a radiopaque guideline or marker to provide means for viewing the implanted device fluoroscopically. The marker may extend the length of the device. Other patterns for markers may also be employed. Radiopaque markers assist the physician to visualize the device both during and after implantation. The marker helps show the physician that the device is properly positioned.

Figure 26:
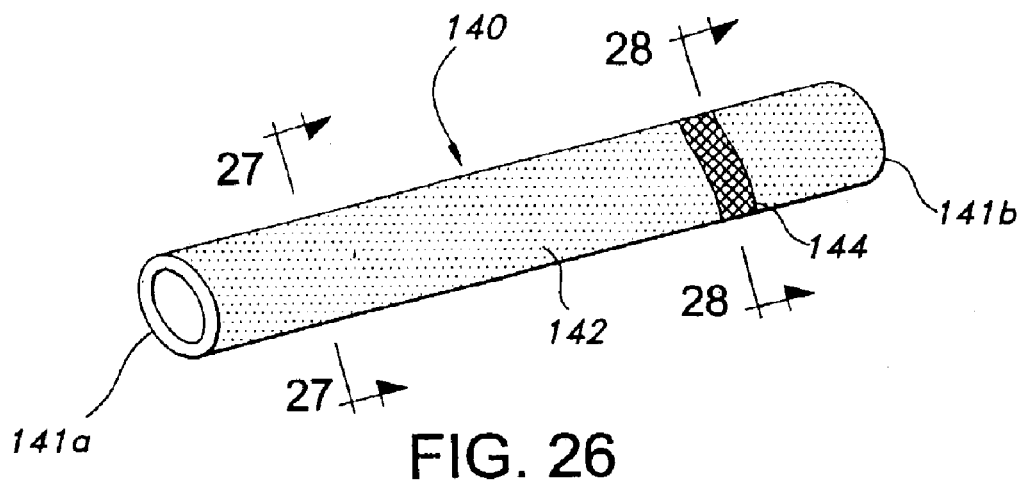
FIG. 26 is a perspective view of a percutaneously or orificially placeable drainage tube of the present invention.

In another aspect of the present invention, a drainage tube 140 is depicted in FIG. 26. Drainage tube 140 is a hollow, elongate, and tubular textile. The drainage tube 140 has opposed open ends 141*a* and 141*b* to facilitate drainage of bodily fluids therebetween. Furthermore, the drainage tube 140 contains a textile portion 142 which is substantially fluid-tight and a textile portion 144 which is not fluid tight. The textile portion 144 is useful for providing additional portions through which bodily fluids may drain into the drainage tube 140. The textile portions 142 and 144 are formed from interlaced biocompatible yarns, as described above. Such a tube with a fluid passage through its wall is not only useful as an intraluminally placeable drainage tube, but is also useful as an intraluminally placeable stent, such as a ureteral stent.

Figure 27:
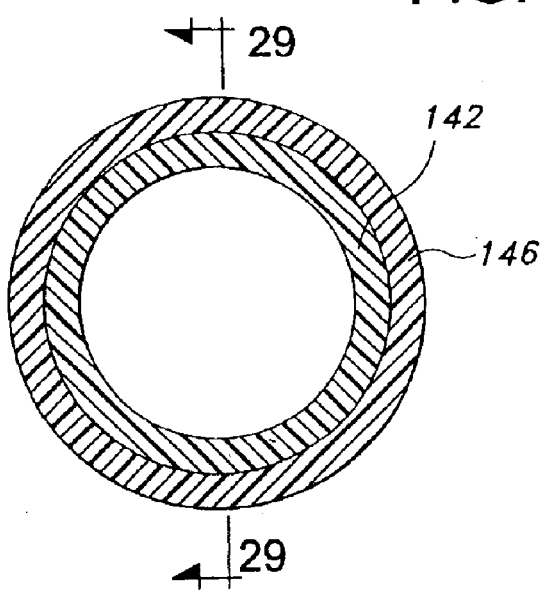
FIG. 27 is a cross sectional view of the tube of FIG. 26 taken along the 27—27 axis.
Figure 28:
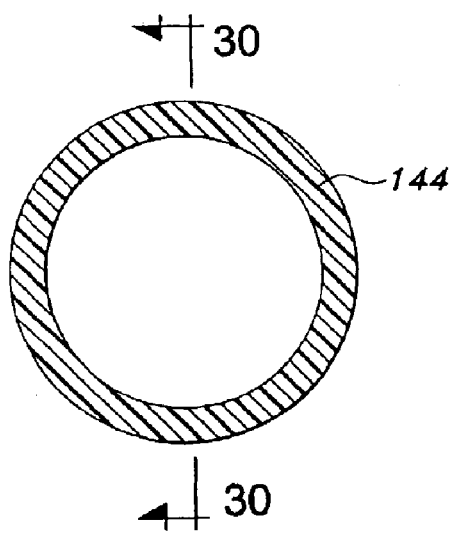
FIG. 28 is a cross sectional view of the tube of FIG. 26 taken along the 28—28 axis.

As depicted in FIG. 27, the textile portion 142 may be covered with a polymeric tube 146. Polymeric tube 146 is desirably made a biocompatible polymer or materials, as described above. Moreover, polymeric portion 146 may be provided by any of the above-described techniques, including the fusing of polymeric yarns. To facilitate fluid flow, the textile portion 144, as depicted in FIG. 28, typically does not have a polymeric tubular covering thereover. Moreover, the textile portion 144 is not limited to any particular circumferential configuration. For example, the textile portion 144 may traverse the circumference of the drainage tube 140 or may be present in just a partially circumferential arrangement. Moreover, the textile portion 144 is not limited to any particular shape, such as a band as depicted in FIG. 26. Other non-limiting shapes include circles, squares, diamond shape, rectangles and the like.

Figure 29:
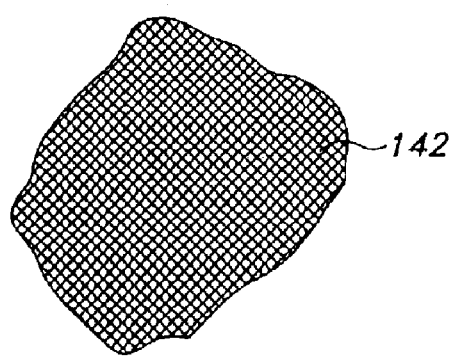
FIG. 29 is an enlarged view of the tube of FIG. 27 taken along the 29—29 axis.
Figure 30:
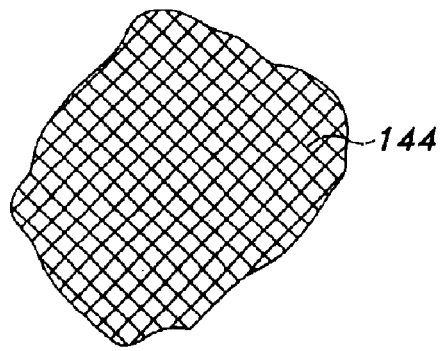
FIG. 30 is an enlarged view of the tube of FIG. 28 taken along the 30—30 axis.

Textile portion 144 may be made non-fluid tight or fluid flowable by a variety of techniques. For example, as depicted in FIGS. 29 and 30, the number of yarns could be reduced in textile portion 144 as compared to textile portions 142 to provide a textile passageway for fluid flow at textile portion 144. Other non-limiting ways to provide a textile passageway for fluid flow at textile portion 144 include varying yarn type, such as reducing yarn density, or altering the interlacing of the yarns, for example angles of yarn intersection, as compared to the other textile portions 142 to permit fluid flow.

Figure 31:
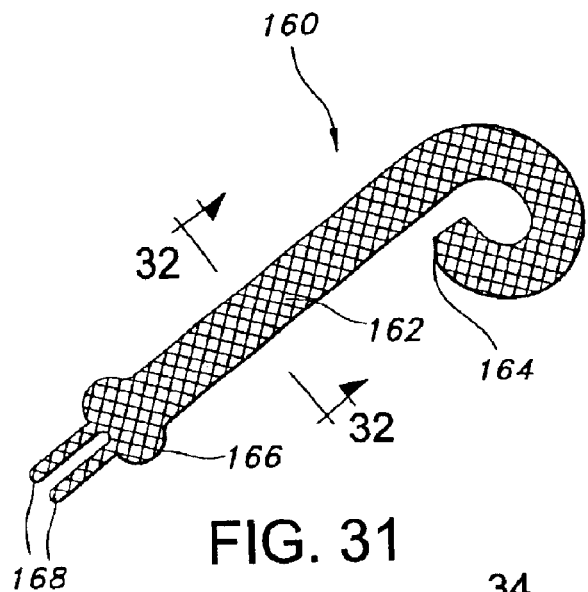
FIG. 31 is a side elevational view of a textile stent of the present invention.

In another aspect of the present invention, a textile stent 160 is depicted in FIG. 31. Textile stent 160 includes an elongate textile tube 162. Textile tube may suitably be made by interlacing the above-described biocompatible yarns by the above-described textile-forming techniques, such as braiding, weaving, knitting and the like. Additionally, stent 160 may include different geometries at one or both of its ends, for instance ends 164 and 166. End 164 has a coil shape or a pig-tail shape which can be useful for anchoring or securing the stent 160 within a bodily organ, such as a kidney. The opposed end 166 may include an outwardly flared or bulbous end for anchoring or securing the stent 160 at a different bodily organ, for instance a bladder. Moreover, stent 160 may include textile tails 168, which are usefully for removal of the stent from the body by a physician. Desirably, stent 160 is a ureteral stent.

Figure 32:
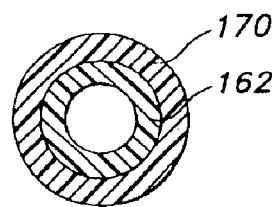
FIG. 32 is a cross sectional view of the stent of FIG. 31 taken along the 32—32 axis.

Furthermore, stent 160 may further include a polymeric tube or coating 170. Such a polymeric tube or coating 170 may be useful in providing, if necessary, a fluid tight covering for the stent. The polymeric tube or covering 170 may be disposed on the exterior surface of the stent 160, as depicted in FIG. 32 may be placed on the interior surface of the stent 160 (not shown). Furthermore, polymeric tube or covering 170 may cover just portions of the stent 160 and need not cover the entire stent 160. For example, portions of the stent 160 proximal to the end 164 may not be covered with the polymeric tube or covering 170 to permit portions threat to be susceptible to fluid flow to facilitate drainage from a bodily organ.

Figure 33:
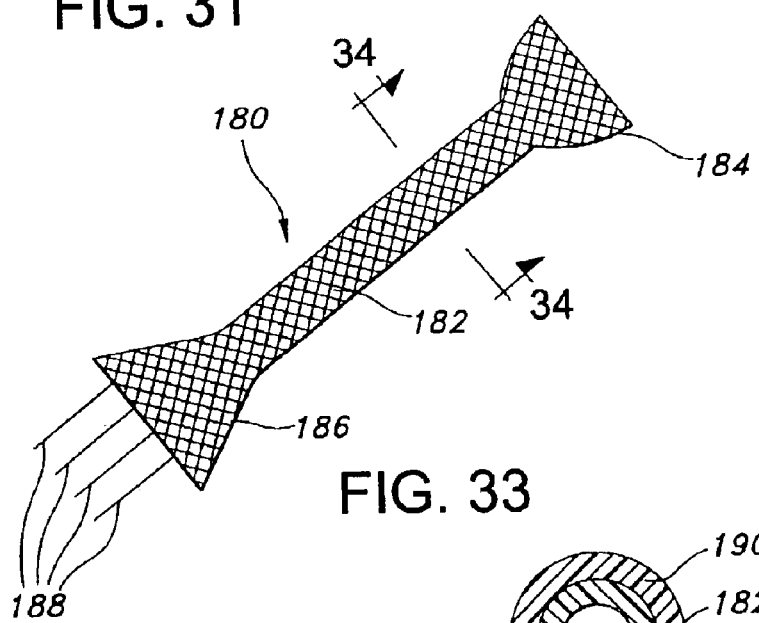
FIG. 33 is a side elevational view of a second textile stent of the present invention.
Figure 34:
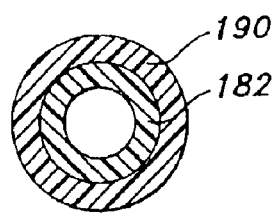
FIG. 34 is a cross sectional view of the second stent of FIG. 33 taken along the 33—33 axis.

FIG. 33 depicts an alternate embodiment of a stent of the present invention. Stent 180 includes an elongate textile tube 182 and outwardly flared ends 184 and 186 for facilitating securement within bodily organs. End 186 may also include tails 188 for facilitating removal of the stent 180 by a physician. As depicted in FIG. 4, stent 180 may also contain a polymeric tube or coating 190, similar to the above-described tube or coating 170. Desirably, stent 180 is a ureteral stent.

Methods of making the intraluminally pushable and placeable devices of the present invention include (i) seamlessly interconnecting yarns in a textile pattern to form an elongate hollow tubular member having a body fluid-contacting luminal surface and a body lumen-contacting exterior surface defining a wall portion therebetween and having an open proximal end and an opposed distal end; and (ii) providing sufficient rigidity to the wall portion such the wall portion is self-supporting to permit the device to be advanced through a body lumen during placement. Desirably, the step of interconnecting the yarns includes braiding the yarns, weaving the yarns, knitting the yarns or filament winding the yarns. Furthermore, the step of providing sufficient rigidity may further include heating portion of the wall portion to fuse a portion of the yarns thereby forming a polymeric, nontextile wall portion.

Method of making the devices of the present invention may further include the step of forming a textile valve in a portion of the tubular member by interlocking yarns which engagingly abut one another to form a fluid tight textile pattern defining a closed quiescent state of the valve and which disengagingly separate to form open areas therebetween defining a non-fluid tight textile pattern defining an open state of the valve. This step of forming the textile valve may include braiding the yarns at a longitudinal angle greater than about 90 degrees or include braiding the yarns at a longitudinal angle less than about 50 degrees.

The above described devices may be suitably used by percutaneously or orificially implanting these devices.

The preferred embodiments having been thus described, it will now be evident to those skilled in the art that further variation thereto may be contemplated. Such variations are not to be regarded as a departure from the invention, the true scope of the invention being set forth in the claims appended hereto.

What is claimed:

1. A catheter comprising:
   an elongate hollow tubular member having a luminal surface and an exterior surface defining a wall portion therebetween and having an open proximal end and an opposed distal end, the wall portion having sufficient self-supporting rigidity to permit the catheter to be advanced through a body lumen;
   a portion of the wall having a textile valve comprising interlocking yarns which engagingly abut one another to form a fluid tight textile pattern defining a closed quiescent state of the valve and which disengagingly separate to form open areas therebetween to form a non-fluid tight textile pattern defining an open state of the valve
   wherein the fluid tight textile pattern is braided textile pattern having the interlocking yarns at a first longitudinal braid angle and the non-fluid tight textile pattern is braided textile pattern having the interlocking yarns at a second longitudinal braid angle, the second longitudinal braid angle being different from the first longitudinal braid angle,
   wherein the textile valve is an infusion valve where upon application of a positive pressure within the tubular member the longitudinal length of the textile valve increases resulting in the second longitudinal braid angle being less than the first longitudinal braid angle, and
   wherein the infusion valve remains in the closed state upon application of a negative pressure within the tubular member.

2. The catheter of claim 1, wherein the open and closed states are responsive to application of a pressure within the hollow tubular member.

3. The catheter of claim 1, wherein the yarns in the fluid tight textile pattern are braided at a longitudinal braid angle of greater than 90 degrees.

4. The catheter of claim 1, wherein said tubular wall portion is a polymeric tubular wall portion.

5. The catheter of claim 1, wherein the yarns are biocompatible synthetic yarns.

6. The catheter of claim 5 wherein the biocompatible synthetic yarns are selected from the group consisting of polyesters, polypropylenes, polyethylenes, polyurethanes, polyamides, polytetrafluoroethylenes, metals and ceramics.

7. The catheter of claim 6, wherein the metal is from the group consisting of stainless steel, platinum, gold, titanium, tantalum and Ni—Co—Cr-based alloy.

8. The catheter of claim 5, wherein the biocompatible synthetic yarns are polyethylene terephthalate yarns.

9. The catheter of claim 1, wherein the yarns are coated with a bio-absorbable composition or a sealant composition.

10. The catheter of claim 1, wherein the yarns releasably contain a drug or a bio-therapeutic agent.

11. The catheter of claim 10, wherein the drug or the bio-therapeutic agent is selected from the group consisting of thrombo-resistant agents antibiotic agents, anti-tumor agents, cell cycle regulating agents, their homologs, derivatives, fragments, pharmaceutical salts, and combinations thereof.

12. A catheter comprising:
   an elongate hollow tubular member having a luminal surface and an exterior surface defining a wall portion therebetween and having an open proximal end and an opposed distal end, the wall portion having sufficient self-supporting rigidity to permit the catheter to be advanced through a body lumen;
   a portion of the wall having a textile valve comprising interlocking yarns which engagingly abut one another to form a fluid tight textile pattern defining a closed quiescent state of the valve and which disengagingly separate to form open areas therebetween to form a non-fluid tight textile pattern defining an open state of the valve, wherein the fluid tight textile pattern is braided textile pattern having the interlocking yarns at a first longitudinal braid angle and the non-fluid tight textile pattern is braided textile pattern having the interlocking yarns at a second longitudinal braid angle, the second longitudinal braid angle being different from the first longitudinal braid angle, and wherein the textile valve is an aspiration valve where upon application of a negative pressure within the tubular member the longitudinal length of the textile valve decreases resulting in the second longitudinal braid angle being greater than the first longitudinal braid angle.

13. The catheter of claim 12, wherein the yarns in the fluid tight textile pattern are braided at a longitudinal braid angle of less than 50 degrees.

14. The catheter of claim 12, wherein the aspiration valve remains in the closed state upon application of a where upon application of a positive within the tubular member.

15. The catheter of claim 12, wherein the open and closed states are responsive to application of a pressure within the hollow tubular member.

16. The catheter of claim 12, wherein said tubular wall portion is a polymeric tubular wall portion.

17. The catheter of claim 12, wherein the yarns are biocompatible synthetic yarns.

18. The catheter of claim 17 wherein the biocompatible synthetic yarns are selected from the group consisting of polyesters, polypropylenes, polyethylenes, polyurethanes, polyamides, polytetrafluoroethylenes, metals and ceramics.

19. The catheter of claim 18, wherein the metal is from the group consisting of stainless steel, platinum, gold, titanium, tantalum and Ni—Co—Cr-based alloy.

20. The catheter of claim 17, wherein the biocompatible synthetic yarns are polyethylene terephthalate yarns.

21. The catheter of claim 12, wherein the yarns are coated with a bio-absorbable composition or a sealant composition.

22. The catheter of claim 12, wherein the yarns releasably contain a drug or a bio-therapeutic agent.

23. The catheter of claim 22, wherein the drug or the bio-therapeutic agent is selected from the group consisting of thrombo-resistant agents, antibiotic agents, anti-tumor agents, cell cycle regulating agents, their homologs, derivatives, fragments, pharmaceutical salts, and combinations thereof.

* * * * *

UNITED STATES PATENT AND TRADEMARK OFFICE
CERTIFICATE OF CORRECTION

PATENT NO. : 6,929,626 B2
DATED : August 16, 2005
INVENTOR(S) : DeCarlo et al.

It is certified that error appears in the above-identified patent and that said Letters Patent is hereby corrected as shown below:

Column 3,
Line 4, should read -- ...which is a braided textile... --.
Line 25, should read -- ...a positive pressure within... --.
Line 45, should read -- ...such that the wall portion... --.

Column 5,
Line 59, should read -- ...such as a kidney or a bladder. --.

Column 7,
Line 14, should read -- ...and its variants refer ... --.
Line 37, should read -- ...comingled, nontextile state. --.

Column 12,
Line 39, should read -- ...may then be placed over a mandrel... --.

Column 14,
Line 32, should read -- ...desirably made of a biocompatible... --.

Column 15,
Lines 3-4, should read -- ...which are useful for removel... --.
Line 17, should read -- ...portions thereat to be... --.

Column 17,
Line 23, should read -- ...application of a positive pressure within... --.

Signed and Sealed this

First Day of November, 2005

JON W. DUDAS
*Director of the United States Patent and Trademark Office*